Figure 1:
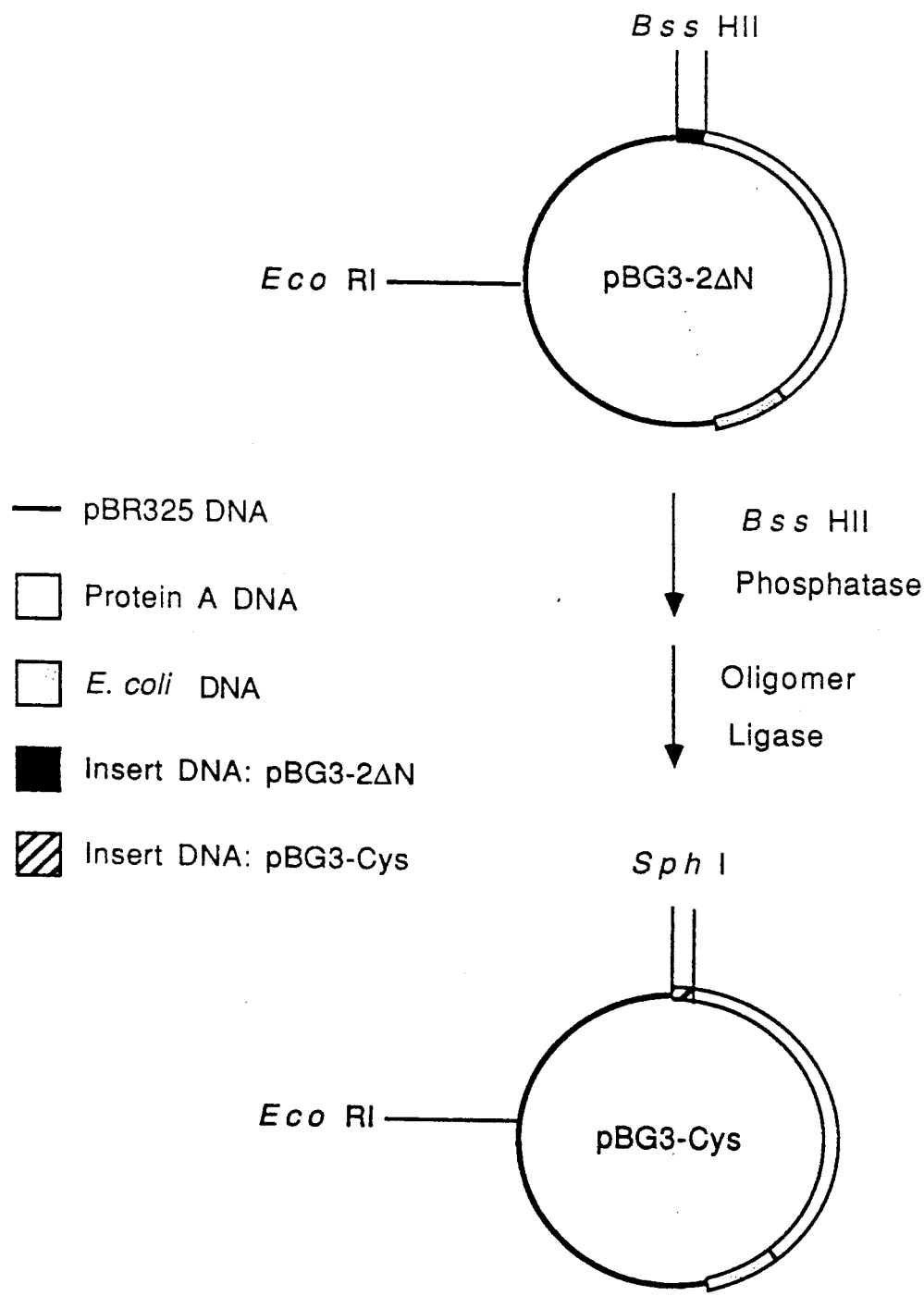

United States Patent [19]

Profy

[11] Patent Number: 5,084,559
[45] Date of Patent: Jan. 28, 1992

[54] PROTEIN A DOMAIN MUTANTS

[75] Inventor: Albert T. Profy, Cambridge, Mass.

[73] Assignee: Repligen Corporation, Cambridge, Mass.

[21] Appl. No.: 32,147

[22] Filed: Mar. 27, 1987

[51] Int. Cl.$^5$ ............................................. C07K 15/04
[52] U.S. Cl. ..................... 530/387; 530/388; 530/403; 530/408; 530/825; 530/413; 530/350; 530/395; 435/69.1; 435/69.7; 435/172.2; 435/172.3; 435/240.2; 935/11; 436/828
[58] Field of Search ............... 435/68, 172.3, 172.1; 530/387, 395, 350, 413, 408; 436/828

[56] References Cited

U.S. PATENT DOCUMENTS

| | | | |
|---|---|---|---|
| 4,430,318 | 2/1984 | Langone | 436/828 |
| 4,479,940 | 10/1984 | Bizzini et al. | 530/404 |
| 4,592,995 | 6/1986 | Hayano et al. | 436/527 |
| 4,705,845 | 11/1987 | Cerami et al. | 530/404 |
| 4,716,122 | 12/1987 | Scheeferse | 436/828 |
| 4,847,325 | 7/1989 | Shadle et al. | 530/351 |
| 4,894,443 | 1/1990 | Greenfield et al. | 530/388 |

OTHER PUBLICATIONS

Lofdahl, S. et al. (1983), "Gene for Staphylococcal Protein A", Proc. Natl. Acad. Sci. U.S..A. 80:697–701.

Colbert, D. et al. (1984), "Molecular Organization of the Protein A Gene and Its Expression in Recombinant Host Organisms", Jour. of Biol. Response Modifiers 3:255–259.

Langone, J. J. (1982), "Applications of Immobilized Protein A in Immunochemical Techniques", J. Immunol. Methods 55:277–296.

Fersht, A. R., and A. J. Wilkinson (1985), "Fine Structure–Activity Analysis of Mutations at Position 51 of Tyrosyl-tRNA Synthetase", Biochemistry 24:5858–5861.

Matheson, N. R., H. L. Gibson, R. A. Hallewell, P. J. Barr, and J. Travis (1986), "Recombinant DNA-Derived Forms of Human Alpha$_1$-Proteinase Inhibitor", The Journal of Biological Chemistry 261(22):10404–10409.

Sauer, R. T., K. Hehir, R. S. Stearman, M. A. Weiss, A. Jeitler-Nilsson, E. G. Suchanek, and C. O. Pabo (1986), "An Engineered Intersubunit Disulfide Enhances the Stability and DNA Binding of the N-Terminal Domain of Lambda Repressor", Biochemistry 25:5992–5998.

Perry, L. J. and R. Wetzel (1986), "Unpaired Cysteine-54 Interferes with the Ability of an Engineered Disulfide to Stabilize T4 Lysozyme", Biochemistry 25:733–739.

Hurle, M. R., N. B. Tweedy, and C. R. Matthews (1986), "Synergism in Folding of a Double Mutant of the Alpha Subunit or Tryptophan Synthase", Biochemistry 25:6356–6360.

Wells, J. A., and D. B. Powers (1986), "In Vivo Formation and Stability of Engineered Disulfide Bonds in Subtilisin", The Journal of Biological Chemistry 261(14):6564–6570.

Sigal, I.S., B. G. Harwood, and R. Arentzen (1982), "Thiol-Beta-Lactamase: Replacement of the Active--Site Serine of RTEM Beta-Lactamase by a Cysteine Residue", Proc. Natl. Acad. Sci. U.S.A. 79:7157–7160.

Ghosh, S. S., S. C. Bock, S. E. Rokita, and E. T. Kaiser (1986), "Modification of the Active Site of Alkaline Phosphatase by Site-Directed Mutagenesis", Science 231:145–148.

Moks et al, Eur. J. Bioch., 156, 637-43, (1986).

Primary Examiner—Esther L. Kepplinger
Assistant Examiner—Jeff Kushan
Attorney, Agent, or Firm—Saliwanchik & Saliwanchik

[57] ABSTRACT

The subject invention concerns novel protein A or protein A-like molecules that can be coupled to other materials through a single, defined site on the protein A molecule. Specifically exemplified is Cysteinyl-rProtein A TM. The compounds of the invention, for example, Cysteinyl-rProtein A TM, can be used in processes wherein protein A is used.

2 Claims, 1 Drawing Sheet

PROTEIN A DOMAIN MUTANTS

BACKGROUND OF THE INVENTION

Protein A is a cell surface protein found in *Staphylococcus aureus*. It has the property of binding the Fc region of mammalian antibodies of class IgG, but the affinity varies with host species and antibody subclass. (For a comprehensive review, see Langone, J. J. [1982] Advances in Immunology 32:157–252.) Protein A can be isolated directly from Staphylococcus cell walls, or from the growth media of mutant strains that secrete protein A. In addition, the gene for protein A has been cloned and expressed in *Escherichia coli* (Lofdahl, S., Guss, B., Uhlen, M., Philipson, L. and Lindberg, M. [1983] Proc. Natl. Acad. Sci. USA 80:697–701; Colbert, D., Anilionis, A., Gelep, P., Farley, J., and Breyer, R. [1984] J. Biological Response Modifiers 3:255–259). This has allowed the production of large amounts of recombinant protein A.

Several applications based on the IgG binding properties of protein A have been developed. These include the following:

Fractionation and purification of antibodies

Protein A has been used for the fractionation of antibodies from sera, and for the purification of monoclonal antibodies. For these purposes, protein A is coupled to a solid matrix such as crosslinked agarose, TRISACRYL TM (distributed by LKB Instruments, Gaithersburg, MD), or silica-based materials (Langone, J.J. [1982]J. Immunol. Methods 55:277–296).

Therapeutic plasma exchange (TPE)

There is evidence that the removal of circulating immune complexes from blood plasma by their binding to protein A has a therapeutic effect on certain autoimmune and malignant diseases (Salinas, F.A. and Hanna, M.G. [1985]Contemporary Topics in Immunobiology, Plenum Press, NY, Vol. 15, Immune Complexes and Human Cancer). To accomplish this, plasma is passed over a device that consists of protein A attached to an inert, nontoxic support.

Immunochemical procedures

Protein A can be used as a probe for IgG in a number of immunochemical procedures, such as enzyme-linked immunosorbant assays (ELISAs). ELISA requires that protein A be coupled to another protein, such as alkaline phosphatase or horseradish peroxidase (Langone, J.J. [1982]J. Immunol. Methods 55:277–296).

Histochemical procedures

Protein A can be used in histochemical or cytological procedures, such as studies of cell surface antigens. For these uses, protein A is often coupled to a fluorescent label, such as by reaction with fluorescein isothiocyanate.

It is clear from the above discussion that for most uses, protein A must be coupled by covalent bonds to other substances. Although a number of coupling chemistries have been devised, most lead to linkage through a protein A amino group. The exact site of attachment, however, is ambiguous. Protein A contains about fifty amino groups of similar reactivity, and any one or several of these can be involved in coupling. This ambiguity has the following practical disadvantages:

(1) Coupling may occur through an amino group that is required for the antibody binding function of protein A. Even if the group is not involved directly, immobilization through it may disrupt the structure of an Fc binding region.

(2) Protein A may be linked through several sites. Although none of the individual sites are required for antibody binding, coupling through several sites could limit the flexibility of the protein A molecule and thereby reduce its ability to bind antibody.

(3) The coupled product is not homogeneous. Thus, when linked to a solid support, different molecules may have different affinities for antibody, depending on the site of immobilization. This would be disadvantageous for applications such as affinity chromatography where antibodies are separated from contaminating substances. Similarly, fluorescent labeling of protein A will afford a mixture of products. This can lead to irreproducible results in immunoassays.

BRIEF SUMMARY OF THE INVENTION

The subject invention concerns a novel protein A or protein A-like molecule that can be coupled to other materials through a single, defined site on the protein A molecule. This protein A or protein A-like molecule is the product of a recombinant protein A gene that has been modified to express a protein containing a single cysteine amino acid residue at a defined position in the amino acid sequence. The novel protein A-like molecule, exemplified herein, is referred to as Cysteinyl-rProtein A TM (Trademark of Repligen Corporation, Cambridge, MA) (Chart A). The nucleotide sequence encoding Cysteinyl-rProtein A TM is shown in Chart B.

The protein A gene codes for five antibody binding domains, (E, A, B, C, and D) and a C-terminal region (or "X" region) that does not bind antibodies (Colbert, D. et al., supra). The X region includes amino acid Glu-310 and all following amino acids in Chart A. The invention consists of modifying the gene such that a cysteine residue is expressed in the C-terminal X region. Any one of the antibody binding regions or a combination thereof can be expressed with the modified C-terminal region to give a protein A-like molecule containing a unique cysteine residue.

Reference to Drawings and Charts

CHART A: Amino acid sequence of Cysteinyl-rProtein A TM

CHART B: Nucleotide sequence of Cysteinyl-rProtein A TM

CHART C: Sequence of 26-basepair insert

CHART D: New oligonucleotide duplex inserted into BssHII-restricted pBG3-2ΔN

FIG. 1: Procedure used to construct a novel plasmid (pBG3-Cys) that expresses Cysteinyl-rProtein A TM

DETAILED DISCLOSURE OF THE INVENTION

Protein A contains no cysteine residues in its amino acid sequence. See Colbert, D. et al. (1984) Jour. of Biological Response Modifiers 3:255–259. Cysteinyl-rProtein A TM was prepared by altering a recombinant protein A gene, expressing the gene in an *E. coli* host, and purifying the recombinant product. The procedure used to construct the altered protein A gene is outlined in FIG. 1. Plasmid pBG3-2ΔN contains a 323-basepair (bp) sequence from an *E. coli* protein, a 1161-bp sequence of the *S. aureus* protein A gene, a 26-bp synthetic DNA sequence that contains a stop codon for the protein A gene, and a 3722-bp sequence from the well-known plasmid pBR325. The synthetic insert contains two BssHII restriction sites that are found nowhere else in pBG3-2ΔN. The gene was modified by restricting plasmid pBG3-2ΔN with BssHII, and replacing the excised insert with a new synthetic insert containing a codon for a cysteine residue.

Plasmid pBG3-2ΔN, in an *E. coli* host, is on deposit with the Agricultural Research Culture Collection (NRRL), Northern Regional Research Center, U.S. Department of Agriculture, 1815 North University Street, Peoria, Ill. 61604, USA. The accession number is NRRL B-15910. The plasmid can be removed from this host by standard procedures, for example, by using cleared lysate-isopycnic density gradient procedures, and the like.

The sequence of the new synthetic insert was selected as follows. The sequence of the 26-bp insert in pBG3-2ΔN is shown in Chart C, where the positions of the BssHII restriction sites and the corresponding amino acid sequence are indicated. The C-terminal amino acid residue of the recombinant protein A expressed from pBG3-2ΔN is serine. This residue was replaced by a cysteine residue in Cysteinyl-rProtein A TM. Because the pKa of the sulfhydryl group of a C-terminal cysteine residue is higher than that of an internal cysteine residue, the terminal group will be less reactive. Therefore, for Cysteinyl-rProtein A TM, a new glycine residue was inserted C-terminal to the cysteine. However, this glycine residue is not considered to be critical. Further, other amino acids can be adjacent to the cysteine. The desired amino acid sequence of the C-terminal region, and one DNA sequence that will express this, are shown in Chart D. The DNA sequence shown was inserted into the BssHII-restricted plasmid pBG3-2ΔN, and thus replaced the 16-bp BssHII fragment shown in Chart C. Note that the DNA sequence in Chart D is a palindrome. This has the following advantages: The DNA is self-complementary, so only one strand of the inserted duplex need be synthesized; and the synthetic duplex can be inserted in either of the two possible orientations to give the desired DNA sequence. In addition, the DNA sequence shown in Chart D contains two SphI restriction sites. No such sites are found in pBG3-2ΔN, so the presence of the insert in a recombinant molecule can be tested by the ability of restriction endonuclease SphI to cleave the molecule.

Before detailing the construction of the recombinant plasmid that expresses Cysteinyl-rProtein A TM, the purification of Cysteinyl-rProtein A TM, and the uses of Cysteinyl-rProtein A TM, the general methods employed are disclosed.

(1) *E. coli* strains

All *E. coli* strains disclosed are *E. coli* K-12 derivatives. Strains *E. coli* JM105, *E. coli* JM103, and *E. coli* PR13 (F−, pnp-13, rna-19, thr-1, leuR6, thi-1, lacY1, xyl-7, mtl-2, malA1, strA132) are well known in the art and can be obtained from known culture repositories or commercial sources. For example, *E. coli* JM105 has the deposit number NRRL B-18067, and *E. coli* JM103 has the deposit number NRRL B-39403.

CULTURE DEPOSITS

The following deposit of a culture disclosed in this application has been made in the Agricultural Research Culture Collection (NRRL), Northern Regional Research Center, U.S. Department of Agriculture, 1815 North University Street, Peoria, Ill. 61604, USA.

| Culture | Repository No. | Deposit Date |
| --- | --- | --- |
| *E. coli* PR13(pBG3-Cys) | NRRL B-18194 | Mar. 17, 1987 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

(2) *E. coli* cultures

Cultures were grown in YT medium (8 g tryptone, 5 g yeast extract, and 5 g NaCl per liter). When required, chloramphenicol was added to a concentration of 30 μg/ml. For the preparation of plates, agar was added to the medium to a concentration of 1.5%.

(3) Preparation of plasmid DNA

Plasmids were prepared from *E. coli* cultures using a modification of the rapid-boiling procedure of Holmes and Quigley (Holmes, D.S. and Quigley, M. [1981], Analytical Biochemistry 114:193–197). Five-ml cultures are grown at 37° C. overnight and pelleted. The pelleted cells are resuspended in 0.4 ml of STET buffer (8% sucrose, 5% TRITON ® X-100 [Rohm & Haas Co., Philadelphia, Pa.]50 mM Tris(hydroxymethyl) amino methane-HCl, pH 8.0, 50 mM ethylenediaminetetraacetic acid [EDTA]). Thirty μl of lysozyme (10 mg/ml water) is added and the mixture placed in a boiling water bath for 2 min. The mixture is then centrifuged (10,000 g, 10 min), the solids are removed, and the supernatants treated with an equal volume of isopropanol. After standing at −10° C. for 10 min, the solids are pelleted by centrifugation (10,000 g, 15 min) and the supernatants discarded. The pellets are dissolved in 75 μl of TE buffer (10 mM Tris-HCl, pH 8.0, 0.5 mM EDTA) and treated with 75 µl of 7.5 ammonium acetate. After standing for 10 min at 4° C. the solids are pelleted by centrifugation (10,000 g, 15 min) and the supernatants removed and treated with 3 volumes of ethanol. After standing for 10 min at −10° C., the precipitated plasmid DNA is pelleted by centrifugation (10,000 g, 15 min), washed with ethanol, and air dried. The pellet is dissolved in 50 µl of TE and stored frozen at −20° C.

(4) Restriction endonuclease digestions

Restriction endonuclease digestions were performed using the procedures recommended by the manufacturer. The buffer used was 10 mM Tris-HCl, pH 7.5, 10 mM $MgCl_2$, 75 mM NaCl, and 100 µg/ml bovine serum albumin.

(5) Electrophoretic separation of DNA fragments

Restriction fragments were separated by electrophoresis on 1% agarose gels in TBE buffer (90 mM Tris base, 0.89 M boric acid, 2 mM EDTA) containing 0.5 µg/ml ethidium bromide. Fragments were visualized by illumination with ultraviolet light and their sizes measured by reference to fragments of known size.

(6) Preparation of competent E. coli cells

Cultures of *E. coli* were grown at 37° C. with agitation until the absorbance at 600 nm was 0.3. The cells were then chilled on ice, pelleted by centrifugation (4100 g, 10 min), resuspended in ½ the original volume of ice-cold 50 mM $CaCl_2$, and incubated on ice for 20 min. The cells were collected by centrifugation as above and resuspended in 1/25 the original volume of ice-cold 50 mM $CaCl_2$. One-ml aliquots were stored frozen at −80° C.

(7) Transformation of competent cells

Frozen competent cells were thawed and 0.2 ml were treated with approximately 0.4 µg of plasmid DNA in 5-20 µl of TE. After standing for 30 min on ice, the mixture was placed in a 37° C. water bath for 2 min and then treated with 1 ml of YT medium and incubated 1 h at 37° C. The cultures were then plated on YT medium containing 30 µg/ml chloramphenicol and grown at 37° C.

(8) Polyacrylamide gel electrophoresis (SDS-PAGE)

Electrophoresis was performed on polyacrylamide gels in the presence of sodium dodecyl sulfate (SDS) as described by Laemmli (Laemmli, U.K. [1970]Nature [London]227:680–685). Slab gels were 1.5 mm thick and contained a total acrylamide concentration of 12%. Samples (up to 25 µl) were mixed with 25 µl of sample buffer (62.5 mM Tris-HCl, pH 6.8, 2% SDS, 5% 2-mercaptoethanol, 10% glycerol, and 0.0025% bromphenol blue), placed in a boiling water bath for 2 min, cooled, and loaded on the gel. Electrophoresis was performed at 75 mA in an apparatus purchased from Hoeffer Scientific Instruments (San Francisco, CA). Gels were stained with a solution of 0.5 g/l coomassie blue in 5:5:1 methanol/water/acetic acid and destained in 7.5% acetic acid.

(9) Synthesis and phosphorylation of oligodeoxyribonucleotide

The oligonucleotide dCGCGCATGCGG-CTAGCCGCATG was synthesized using an Applied Biosystems (Foster City, CA) model 380A DNA Synthesizer using the phosphoramidite procedure recommended by the manufacturer. The deprotected oligomer was purified using the electrophoretic method of Atkinson and Smith (Atkinson, T. and Smith, M. [1984]in Oligonucleotide Synthesis: A Practical Approach, Gait, M.J., Ed. IRL Press, Arlington, VA, pp. 35-81.) The purified oligomer (29 µg) was treated with 10 units of T4 polynucleotide kinase in 30 µl of 50 mM Tris-HCl, pH 7.6, 10 mM $MgCl_2$, 5 mM dithiothreitol (DTT), 0.1 mM spermidine, 0.1 mM EDTA, and 0.15 M adenosine triphosphate (ATP). The solution was incubated for 30 min at 37° C. and then the DNA was precipitated with 1/10 volume of 3 M sodium acetate, pH 4.7, and 3 volumes of ethanol (−10° C., 10 min). The DNA was pelleted by centrifugation (10,000 g, 15 min), washed with ethanol, and dried. The pellet was redissolved in 30 µl of TE, heated to 60° C., and cooled slowly to room temperature in order to form a DNA duplex.

Following are examples which illustrate procedures for practicing the invention. These examples should not be construed as limiting. All percentages are by weight and all solvent mixture proportions are by volume unless otherwise noted.

EXAMPLE 1

BssHII endonuclease digestion of plasmid pBG3-2ΔN

One µg of pBG3-2ΔN was incubated with 12 units of BssHII in the buffer described above in (4) for 120 min at 37° C. One µl (20 units) of alkaline phosphatase (calf intestine) was added and the solution incubated for an additional 1 h at 37° C. The solution was then diluted to 100 µl with TE, extracted with two 50-µl portions of phenol, extracted with two 100-µl portions of diethyl ether, treated with 1/10 volume of 3 M sodium acetate (pH 4.7), and precipitated with 3 volumes of ethanol. The restricted, phosphorylated DNA was pelleted by centrifugation (10,000 g, 15 min), washed with ethanol, dried, and dissolved in 30 µl TE.

EXAMPLE 2

Ligation of oligonucleotide insert

The dephosphorylated BssHII restriction fragments of pBG3-2ΔN (0.5 µg), the synthetic oligonucleotide duplex described in (9) (5 µg), and T4 DNA ligase (400 units) were incubated in 50 mM Tris-HCl, pH 7.8, 6 mM $MgCl_2$, 20 mM DTT containing 1 mM ATP for 15 h at 16° C. The reaction mixture was used to transform competent *E. coli* JM105 cells as described above in (7).

EXAMPLE 3

Screening of transformants for new SphI restriction sites

Plasmid DNA was isolated from 10 colonies of transformants from Example 2. This DNA was restricted by a mixture of SphI and EcoRI. Agarose electrophoresis revealed the fragments that would be expected from the insertion of the DNA sequence shown in Chart D into the BssHII restriction fragment of pBG3-2ΔN, namely, one of 1.2 kbp and one of 4.0 kbp. Plasmid DNA from all 10 of the transformants tested gave these fragments on digestion. By contrast, plasmid pBG3-2ΔN gave, as expected, only a single fragment of 5.2 kbp. The plasmid isolated from the transformants was designated pBG3-Cys.

EXAMPLE 4

Transformation of *E. coli* PR13 with pBG3-Cys

Plasmid pBG3-Cys from one of the transformants described in Example 3 was used to transform competent *E. coli* JM103 cells. Plasmid isolated from 4 of the *E. coli* JM103(pBG3-Cys) transformants was screened for the SphI site as described in Example 3, and all were found to contain it. Plasmid from 1 of these transformants was used to transform competent *E. coli* PR13 cells. Plasmid was isolated from 4 of the *E. coli* PR13(pBG3-Cys) transformants and screened for the presence of the SphI site. All 4 were found to contain the site.

EXAMPLE 5

Expression of Cysteinyl-rProtein A TM by *E. coli* PR13(pBG3-Cys)

Cultures of *E. coli* PR13(pBG3-Cys) and *E. coli.* PR13(pBG3-2ΔN) were grown overnight at 37° C. and 50 μl of each was pelleted. The pellets were suspended in 25 μl of sample buffer and subjected to SDS-PAGE as described in (8). The destained gel showed that the *E. coli* PR13(pBG3-Cys) cultures express a protein of the same apparent molecular weight and in the same amount as the recombinant protein A known to be expressed by *E. coli* PR13(pBG3-2ΔN).

EXAMPLE 6

Large-scale fermentation of *E. coli* PR13(pBG3-Cys)

Ten ml of an overnight culture of *E. coli* PR13(pBG3-Cys) in YT containing 30 μg/ml chloramphenicol was used to inoculate 10 L of modified 2% medium (20 g/L yeast extract, 20 g/L casamino acids, 20 g/L casein peptone, 2 g/L $K_2HPO_4$, 2 g/L $KH_2PO_4$, 2 g/L $Na_2HPO_4 \cdot 7H_2O$) containing 10 mg/L chloramphenicol in a 201 Chemapec fermenter (Chemapec, Inc., Woodbury, NY). The recombinant cells were grown at 37° C. with 50 dissolved $O_2$. The pH was maintained at 6.81 with 85% lactic acid and 50% NaOH. Foam was controlled by the addition of ANTIFOAM B (E.I. DuPont de Nemours & Co., Inc., Wilmington, DE). Cells were harvested in late log phase by centrifugation (3,500 xg, 20 min). Cell yields were 30 g wet cell weight (wcw) per liter.

EXAMPLE 7

Lysis of recombinant cells

Harvested *E. coli* PR13(pBG3-Cys) cells (150 g) were suspended in 1 L of lysis buffer (10 mM Tris-HCl, pH 8.3, 5 mM EDTA, 1 mM DTT, 0.1 mM phenylmethylsulfonyl fluoride [PMSF], and 0.5% TRITON® X-100). Lysis was performed by passing the suspension 2 times through a Dynomill model KDL-Pilot (Impandex, Maywood, NJ) charged with 1.2 L of glass beads (0.5–0.7 mm diameter). The lysate was clarified by centrifugation (7,310 g, 45 min).

EXAMPLE 8

Purification of Cysteinyl-rProtein A TM

An 11×13 cm column of DEAE-SEPHAROSE FAST FLOW (Pharmacia Fine Chemicals, Piscataway, NJ) was equilibrated with wash buffer (35 mM Tris-HCl, pH 8.3, 2 mM EDTA, 1 mM DTT, 0.1 mM PMSF) and 1.5 L of clarified lysate (Example 7) was passed over the column at a flow rate of 100 ml/min. Wash buffer (3 L) was then passed over the column at 100 ml/min. The flow rate was then reduced to 10 ml/min, and Cysteinyl-rProtein A TM was eluted by a linear gradient formed from 4 L of wash buffer and 4 L of elution buffer (wash buffer containing 200 mM KCl). Two-hundred-ml fractions were collected, and samples from each fraction were analyzed by SDS-PAGE. Those containing a protein of 40 kilodalton (kd) apparent molecular weight (Cysteinyl-rProtein A TM) were pooled and heated to 85° C. for 10 min. Precipitated contaminants were pelleted by centrifugation (7,310 g, 30 min) and the supernatant was passed through a 0.45-micron filter. The filtrate was treated with 3 volumes of ethanol and stirred for 30 min at room temperature. The resulting precipitate was collected by centrifugation (7,310 g, 30 min) and dried. The pellet was dissolved in sterile TE and stored at 4° C. in the presence of 1 mM DTT. The 40 kd product was judged to be >90% pure by SDS-PAGE. The yield, as measured by absorbance at 275 nm, was 5 mg per g wcw.

EXAMPLE 9

Fluorescein-labeled protein A

The reagent fluorescein-5-maleimide (available from Molecular Probes, Inc., Eugene, OR) reacts with sulfhydryl groups of proteins to form stable covalent bonds. Cysteinyl-rProtein A TM (28 μg) and fluorescein-5-maleimide (16 μg) were incubated in 25 μl of 0.1 M sodium phosphate, pH 7.5, 0.5 mM EDTA for 30 min at 37° C. The solution was subjected to SDS-PAGE as described above (8) and the fluorescent products visualized by illumination with ultraviolet light before coomassie staining. This revealed an intensely fluorescent protein of 40 kd molecular weight corresponding to Cysteinyl-rProtein A TM. Under the same conditions, recombinant protein A from *E. coli* PR13(pBG3-2ΔN) showed a product with little or no fluorescence.

The product of the reaction of Cysteinyl-rProtein A TM and fluorescein-5-maleimide was passed over a column of human IgG immobilized to agarose (Mayes, E.L.V. [1984]in Methods in Molecular Biology, Volume 1, Proteins, Walker, J.M. Ed. Humana Press, Cliffton, NJ, pp. 13–20). The fluorescent product was bound by the column and not eluted by extensive washing with phosphate-buffered saline (PBS). The fluorescent protein was eluted by 0.2 M glycine, pH 2.0, as would be expected for a protein A-like material. A 40 kd, fluorescent protein was revealed by SDS-PAGE of the column eluate.

EXAMPLE 10

Coupling of Cysteinyl-rProtein A TM to thiol affinity materials

ACTIVATED THIOL SEPHAROSE 4B (Pharmacia Fine Chemicals) is a gel that reacts with reduced sulfhydryl groups to form stable, covalent disulfide bonds. Cysteinyl-rProtein A TM (2 mg) in 0.5 ml of 0.1 M sodium phosphate, pH 7.5, 0.5 mMEDTA was mixed with 0.5 ml of swelled ACTIVATED THIOL SEPHAROSE 4B and turned for 2 h at room temperature. The gel was washed with PBS until no protein was observed in the wash. The gel was then treated with 10 mM DTT in order to reduce the disulfide bonds and thereby release the bound proteins. Approximately 1 mg of a 40 kd protein was liberated per ml of gel, as measured by SDS-PAGE. When the experiment was performed using the recombinant protein A expressed by *E. coli* PR13(pBG3-2ΔN), no protein was released from the gel by DTT treatment.

The nucleotide sequence encoding Cysteinyl-rProtein A TM can be prepared by a "gene machine" by procedures well known in the art. This is possible because of the disclosure of the nucleotide sequence.

Cysteinyl-rProtein A TM can be chemically synthesized by solid phase peptide synthetic techniques such as BOC and FMOC (Merrifield, R.B. [1963] J. Amer. Chem. Soc. 85:2149: Chang, C. and Meinenhofer, J. [1978] Int. J. Peptide Protein Res. 11:246).

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively,
QR = AG if S is T or C
J = A or G
K = T or C
L = A, T, C or G
M = A, C or T Key: Each 3-letter deoxynucleotide triPlet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively,
QR = AG if S is T or C
J = A or G
K = T or C
L = A, T, C or G
M = A, C or T The above shows that the novel amino acid sequence of the subject invention can be prepared by nucleotide sequences other than that disclosed herein. Functionally equivalent nucleotide sequences encoding the novel amino acid sequence of Cysteinyl-rProtein A TM, or fragments thereof having protein A-like activity, can be prepared by known synthetic procedures. Accordingly, the subject invention includes such functionally equivalent nucleotide sequences.

In addition it has been shown that proteins of identified structure and function may be constructed by changing the amino acid sequence if such changes do not alter the protein secondary structure (Kaiser, E.T. and Kezdy, F.J. [1984]Science 223:249-255). Thus the subject invention includes mutants of the amino acid sequence depicted herein which do not alter the protein secondary structure, or if the structure is altered, the biological activity is retained to some degree.

As shown above, it is well within the skill of those in the genetic engineering art to use the nucleotide sequence encoding Cysteinyl-rProtein A TM activity of the subject invention to produce proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare Cysteinyl-rProtein A TM of the subject invention by microbial means or mammalian tissue culture technology. Further, the antibody-binding domains of protein A can be prepared by standard gene machine procedures. These domains can be used individually or in various combinations with the X region, disclosed herein, fused thereto. Modification of the X region to code for a cysteine residue can be done before or after fusion to the domain(s) by standard procedures.

The protein A gene also can be modified so as to incorporate a cysteine in the N-terminal coding sequence preceding the IgG binding domain(s). Alternatively, an N-terminal cysteine can be further removed from the IgG binding domain(s) by incorporating a synthetic DNA sequence at the 5' end of the protein A gene to create a polypeptide "spacer" between the cysteine and the IgG binding domain(s). This spacer could be about 1 to about 100 amino acids in length. As disclosed herein, the modification can be made to any of the protein A domains and the domains can be used individually or in various combinations with the modified region fused thereto. These modifications, wherein the cysteine residue is outside the IgG binding regions, can be done readily by a person skilled in the art using standard procedures.

Chart A

Amino Acid Sequence of Cysteinyl-rProtein A ™

| Met | Leu | Arg | Pro | Val | Glu | Thr | Pro | Thr | Arg | Glu | Ile | Lys | Lys |
|---|---|---|---|---|---|---|---|---|---|---|---|---|---|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Ala | Asn | Leu | Leu |
| Ala | Glu | Ala | Lys | Lys | Leu | Asn | Asp | Ala | Gln | Ala | Pro | Lys | Ala |
| Asp | Asn | Lys | Phe | Asn | Lys | Glu | Gln | Gln | Asn | Ala | Phe | Tyr | Glu |
| Ile | Leu | His | Leu | Pro | Asn | Leu | Thr | Glu | Glu | Gln | Arg | Asn | Gly |
| Phe | Ile | Gln | Ser | Leu | Lys | Asp | Asp | Pro | Ser | Val | Ser | Lys | Glu |
| Ile | Leu | Ala | Glu | Ala | Lys | Lys | Leu | Asn | Asp | Ala | Gln | Ala | Pro |
| Lys | *Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Asn | Lys | Asn | Leu | Gly | Lys | Glu | Asp | Gly | Lys | Pro | Gly | Lys | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Gly |
| Arg | Ala | Cys | Gly |

*X region consists of Glu-310 and all amino acids following

Chart B

Nucleotide Sequence of Cysteinyl-rProtein A ™

|  |  |  | CATATGTCAT | GAGAGTTTAT |
|---|---|---|---|---|
| CGTTCCCAAT | ACGCTCGAAC | GAACGTTCGG | TTGCTTATTT | TATGGCTTCT |
| GTCAACGCTG | TTTTAAAGAT | TAATGCGATC | TATATCACGC | TGTGGGTATT |
| GCAGTTTTTG | GTTTTTTGAT | CGCGGTGTCA | GTTCTTTTTA | TTTCCATTTC |
| TCTTCCATGG | GTTTCTCACA | GATAACTGTG | TGCAACACAG | AATTGGTTAA |
| CTAATCAGAT | TAAAGGTTGA | CCAGTATTAT | TATCTTAATG | AGGAGTCCCTT |
|  |  |  |  | ATG |

| TTA | CGT | CCT | GTA | GAA | ACC | CCA | ACC | CGT | GAA | ATC | AAA | AAA | CTC |
|---|---|---|---|---|---|---|---|---|---|---|---|---|---|
| GAC | GGC | CTT | GCG | CAA | CAC | GAT | GAA | GCT | CAA | CAA | AAT | GCT | TTT |
| TAT | CAA | GTG | TTA | AAT | ATG | CCT | AAC | TTA | AAC | GCT | GAT | CAA | CGT |
| AAT | GGT | TTT | ATC | CAA | AGC | CTT | AAA | GAT | GAT | CCA | AGC | CAA | AGT |
| GCT | AAC | GTT | TTA | GGT | GAA | GCT | CAA | AAA | CTT | AAT | GAC | TCT | CAA |
| GCT | CCA | AAA | GCT | GAT | GCG | CAA | CAA | AAT | AAG | TTC | AAC | AAA | GAT |
| CAA | CAA | AGC | GCC | TTC | TAT | GAA | ATC | TTG | AAC | ATG | CCT | AAC | TTA |
| AAC | GAG | GAG | CAA | CGC | AAT | GGT | TTC | ATT | CAA | AGT | CTT | AAA | GAC |
| GAT | CCA | AGC | CAA | AGC | ACT | AAC | GTT | TTA | GGT | GAA | GCT | AAA | AAA |
| TTA | AAC | GAA | TCT | CAA | GCA | CCG | AAA | GCT | GAC | AAC | AAT | TTC | AAC |
| AAA | GAA | CAA | CAA | AAT | GCT | TTC | TAT | GAA | ATC | TTG | AAC | ATG | CCT |
| AAC | TTG | AAC | GAA | CAA | CGC | AAT | GGT | TTC | ATC | CAA | AGC | TTA |
| AAA | GAT | GAC | CCA | AGT | CAA | AGT | GCT | AAC | CTT | TTA | GCA | GAA | GCT |
| AAA | AAG | TTA | AAT | GAA | TCT | CAA | GCA | CCG | AAA | GCT | GAT | AAC | AAA |
| TTC | AAC | AAA | GAA | CAA | CAA | AAT | GCT | TTC | TAT | GAA | ATC | TTA | CAT |
| TTA | CCT | AAC | TTA | AAT | GAA | GAA | CAA | CGC | AAT | GGT | TTC | ATC | CAA |
| AGC | TTA | AAA | GAT | GAC | CCA | AGC | CAA | AGC | GCT | AAC | CTT | TTA | GCA |
| GAA | GCT | AAA | AAG | CTA | AAT | GAT | GCA | CAA | GCA | CCA | AAA | GCT | GAC |
| AAC | AAA | TTC | AAC | AAA | GAA | CAA | CAA | AAT | GCT | TTC | TAT | GAA | ATT |
| TTA | CAT | TTA | CCT | AAC | TTA | ACT | GAA | GAA | CAA | CGT | AAC | GGC | TTC |
| ATC | CAA | AGC | CTT | AAA | GAC | GAT | CCT | TCA | GTG | AGC | AAA | GAA | ATT |
| TTA | GCA | GAA | GCT | AAA | AAG | CTA | AAC | GAT | GCT | CAA | GCA | CCA | AAA |
| GAG | GAA | GAC | AAC | AAC | AAG | CCT | GGT | AAA | GAA | GAC | GGC | AAC | AAA |
| CCT | GGT | AAA | GAA | GAC | GGC | AAC | AAA | CCT | GGT | AAA | GAA | GAC | AAC |
| AAA | AAC | CTT | GGC | AAA | GAA | GAC | GGC | AAC | AAA | CCT | GGT | AAA | GAA |
| GAC | AAC | AAA | AAA | CCT | GGC | AAA | GAA | GAT | GGC | AAC | AAA | CCT | GGT |
| AAA | GAA | GAC | GGC | AAC | AAG | CCT | GGT | AAA | GAA | GAT | GGC | AAC | AAA |
| CCT | GGT | AAA | GAA | GAT | GGC | AAC | AAG | CCT | GGT | AAA | GAA | GAT | GGC |
| AAC | AAG | CCT | GGT | AAA | GAA | GAC | GGC | AAC | GGA | GTC | ATC | GGG | CGC |
| GCA | TGC | GGC | TAG | CCGCATGCGCGCCCG |

Chart C

Sequence of 26-Basepair Insert

Gly Arg Ala Ser Stop

5' C GGG CGC GCT AGC TAG CTA GCG CGC C 3'

-continued
Chart C

3' G CCC GCG CGA TCG ATC GAT CGC GCG G 5'

Bss HII                    Bss HII

Chart D
New Oligonucleotide Duplex Inserted into
BssHF-Restricted pBG3-2ΔN

Arg Ala Cys Gly Stop
5' CGC GCA TGC GGC TAG CCG CAT G 3'

-continued
Chart D

3'  GT ACG CCG ATC GGC GTA CGC GC 5'
       Sph I              Sph I

I claim:

1. A modified protein A consisting essentially of the protein A sequence modified to have a cysteine residue between the Glu$_{310}$ residue and the C-terminus of the protein, wherein said modification is accomplished either
   (a) by changing a single naturally occuring residue of the protein to a cysteine residue through a genetic mutation, or,
   (b) by inserting a single residue of cysteine into the native sequence.

2. Modified protein A having the following amino acid sequence read from N to C terminus:

| Met | Leu | Arg | Pro | Val | Glu | Thr | Pro | Thr | Arg | Glu | Ile | Lys | Lys |
|-----|-----|-----|-----|-----|-----|-----|-----|-----|-----|-----|-----|-----|-----|
| Leu | Asp | Gly | Leu | Ala | Gln | His | Asp | Glu | Ala | Gln | Gln | Asn | Ala |
| Phe | Tyr | Gln | Val | Leu | Asn | Met | Pro | Asn | Leu | Asn | Ala | Asp | Gln |
| Arg | Asn | Gly | Phe | Ile | Gln | Ser | Leu | Lys | Asp | Asp | Pro | Ser | Gln |
| Ser | Ala | Asn | Val | Leu | Gly | Glu | Ala | Gln | Lys | Leu | Asn | Asp | Ser |
| Gln | Ala | Pro | Lys | Ala | Asp | Ala | Gln | Gln | Asn | Lys | Phe | Asn | Lys |
| Asp | Gln | Gln | Ser | Ala | Phe | Tyr | Glu | Ile | Leu | Asn | Met | Pro | Asn |
| Leu | Asn | Glu | Glu | Gln | Arg | Asn | Gly | Phe | Ile | Gln | Ser | Leu | Lys |
| Asp | Asp | Pro | Ser | Gln | Ser | Thr | Asn | Val | Leu | Gly | Glu | Ala | Lys |
| Lys | Leu | Asn | Glu | Ser | Gln | Ala | Pro | Lys | Ala | Asp | Asn | Asn | Phe |
| Asn | Lys | Glu | Gln | Gln | Asn | Ala | Phe | Tyr | Glu | Ile | Leu | Asn | Met |
| Pro | Asn | Leu | Asn | Glu | Glu | Gln | Arg | Asn | Gly | Phe | Ile | Gln | Ser |
| Leu | Lys | Asp | Asp | Pro | Ser | Gln | Ser | Ala | Asn | Leu | Leu | Ala | Glu |
| Ala | Lys | Lys | Leu | Asn | Glu | Ser | Gln | Ala | Pro | Lys | Ala | Asp | Asn |
| Lys | Phe | Asn | Lys | Glu | Gln | Gln | Asn | Ala | Phe | Tyr | Glu | Ile | Leu |
| His | Leu | Pro | Asn | Leu | Asn | Glu | Glu | Gln | Arg | Asn | Gly | Phe | Ile |
| Gln | Ser | Leu | Lys | Asp | Asp | Pro | Ser | Gln | Ser | Ala | Asn | Leu | Leu |
| Ala | Glu | Ala | Lys | Lys | Leu | Asn | Asp | Ala | Gln | Ala | Pro | Lys | Ala |
| Asp | Asn | Lys | Phe | Asn | Lys | Glu | Gln | Gln | Asn | Ala | Phe | Tyr | Glu |
| Ile | Leu | His | Leu | Pro | Asn | Leu | Thr | Glu | Glu | Gln | Arg | Asn | Gly |
| Phe | Ile | Gln | Ser | Leu | Lys | Asp | Asp | Pro | Ser | Val | Ser | Lys | Glu |
| Ile | Leu | Ala | Glu | Ala | Lys | Lys | Leu | Asn | Asp | Ala | Gln | Ala | Pro |
| Lys | Glu | Glu | Asp | Asn | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Asn | Lys | Asn | Leu | Gly | Lys | Glu | Asp | Gly | Asn | Lys | Pro | Gly | Lys |
| Glu | Asp | Asn | Lys | Lys | Pro | Gly | Lys | Glu | Asp | Gly | Asn | Lys | Pro |
| Gly | Lys | Glu | Asp | Gly | Asn | Lys | Pro | Gly | Lys | Glu | Asp | Gly | Asn |
| Lys | Pro | Gly | Lys | Glu | Asp | Gly | Asn | Lys | Pro | Gly | Lys | Glu | Asp |
| Gly | Asn | Lys | Pro | Gly | Lys | Glu | Asp | Gly | Asn | Gly | Val | Ile | Gly |
| Arg | Ala | Cys | Gly. |   |   |   |   |   |   |   |   |   |   |

* * * * *